(12) United States Patent
Kuras

(10) Patent No.: US 7,169,181 B2
(45) Date of Patent: Jan. 30, 2007

(54) ARTIFICIAL DISC

(75) Inventor: James Michael Kuras, Macedonia, OH (US)

(73) Assignee: Axiomed Spine Corporation, Garfield Heights, OH (US)

( * ) Notice: Subject to any disclaimer, the term of this patent is extended or adjusted under 35 U.S.C. 154(b) by 336 days.

(21) Appl. No.: 10/315,373

(22) Filed: Dec. 10, 2002

(65) Prior Publication Data

US 2004/0122517 A1    Jun. 24, 2004

(51) Int. Cl.
*A61F 2/44*    (2006.01)
*A61B 17/56*   (2006.01)

(52) U.S. Cl. .................. 623/17.11; 623/17.16

(58) Field of Classification Search ... 623/17.11–17.16
See application file for complete search history.

(56) References Cited

U.S. PATENT DOCUMENTS

| 5,401,269 | A | * | 3/1995 | Buttner-Janz et al. ... 623/17.15 |
| 5,702,450 | A | * | 12/1997 | Bisserie .................... 623/17.16 |
| 5,893,889 | A | | 4/1999 | Harrington |
| 6,001,130 | A | | 12/1999 | Bryan et al. |
| 6,063,121 | A | * | 5/2000 | Xavier et al. ............. 623/17.15 |
| 6,162,252 | A | | 12/2000 | Kuras et al. |
| 6,315,797 | B1 | | 11/2001 | Middleton |
| 6,533,818 | B1 | * | 3/2003 | Weber et al. ............. 623/17.16 |
| 6,607,558 | B2 | | 8/2003 | Kuras |
| 2002/0035400 | A1 | | 3/2002 | Bryan et al. |
| 2003/0135277 | A1 | * | 7/2003 | Bryan et al. ............. 623/17.12 |
| 2004/0054411 | A1 | * | 3/2004 | Kelly et al. ............... 623/17.13 |
| 2005/0256581 | A1 | * | 11/2005 | Songer et al. ........... 623/17.16 |

FOREIGN PATENT DOCUMENTS

EP    1103237 A2 *   5/2001   ............. 623/17.11

* cited by examiner

*Primary Examiner*—Pedro Philogene
(74) *Attorney, Agent, or Firm*—Tarolli, Sundheim, Covell, & Tummino LLP

(57) ABSTRACT

An artificial disc to replace a damaged spinal disc in a spinal column includes an upper retaining member having an outer surface engageable with a first vertebra of the spinal column and an inner surface. A lower retaining member has an outer surface engageable with a second vertebra of the spinal column and an inner surface. A resilient core interconnects the upper and lower retaining members. The resilient core has an upper surface affixed to the inner surface of the upper retaining member. The resilient core has a lower surface affixed to the inner surface of the lower retaining member. The resilient core has a surface extending from one of the upper and lower surfaces toward another of the upper and lower surfaces and at least partially defining an empty space extending from the one of the upper and lower surfaces.

25 Claims, 4 Drawing Sheets

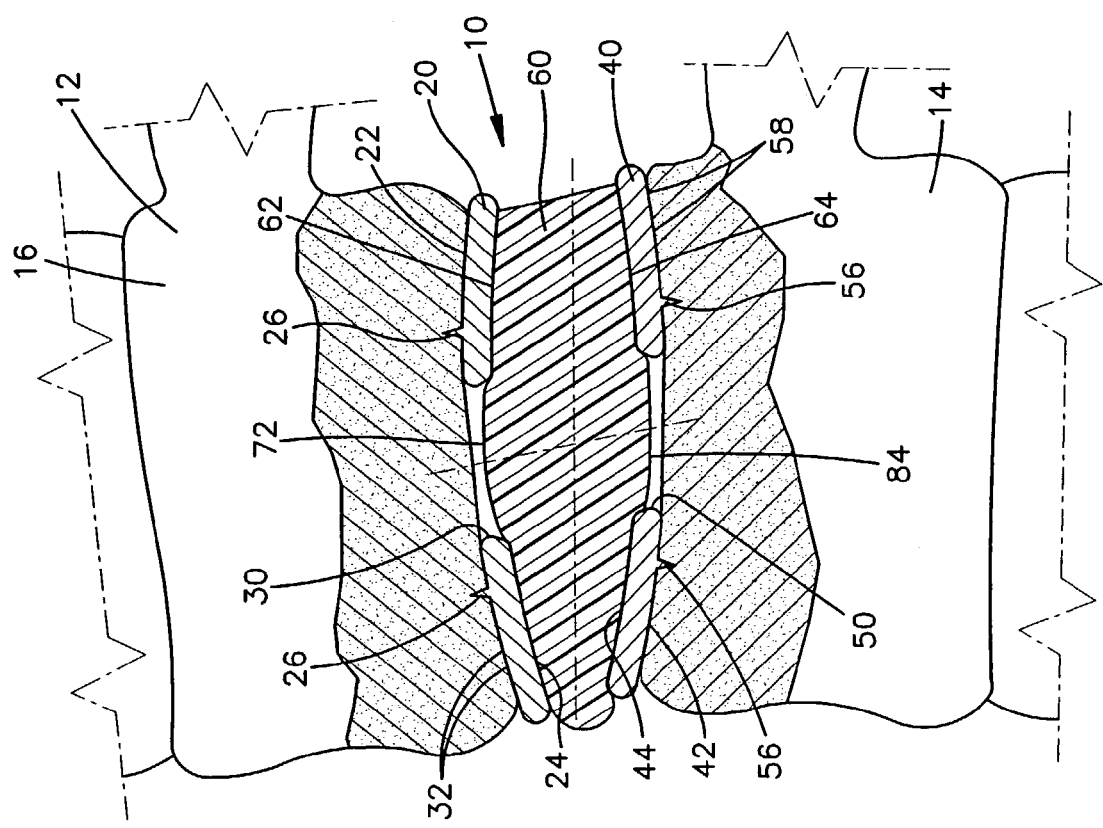
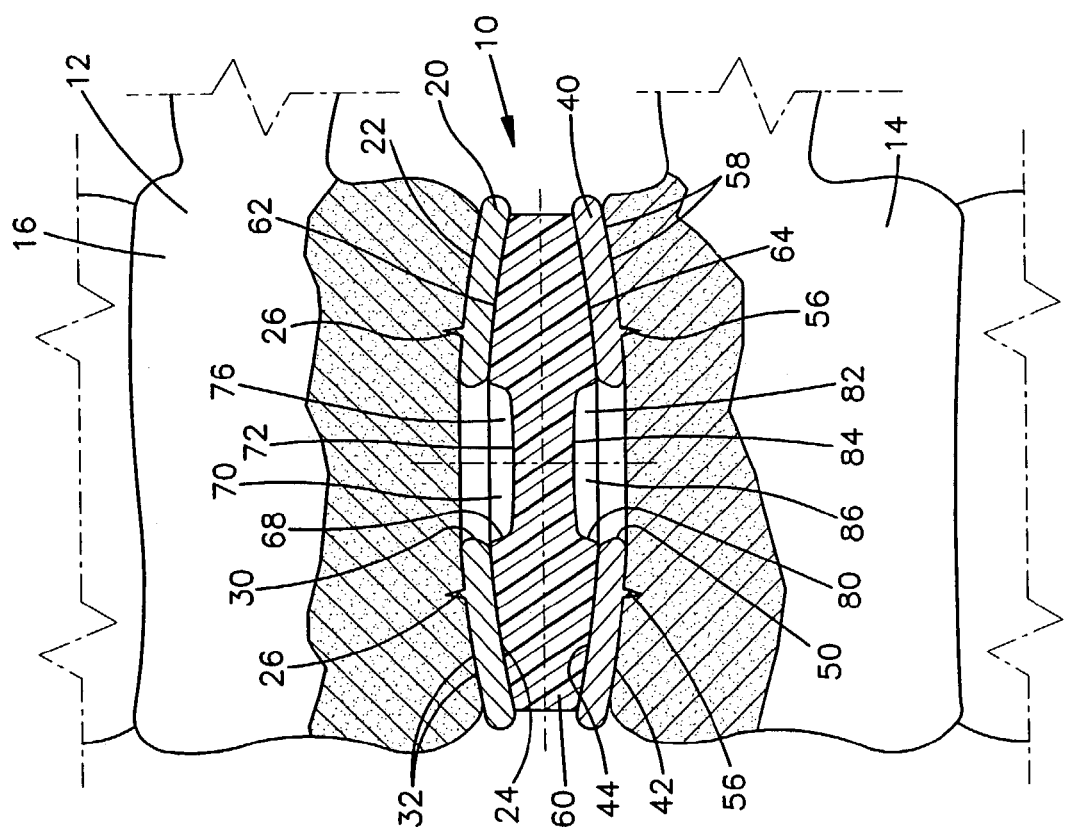

ARTIFICIAL DISC

FIELD OF THE INVENTION

The present invention relates to an artificial disc to replace a damaged spinal disc in a spinal column.

BACKGROUND OF THE INVENTION

A known artificial disc is disclosed in U.S. Pat. No. 5,893,889. U.S. Pat. No. 5,893,889 discloses an artificial disc having upper and lower members for engaging adjacent vertebrae. A spherical pivot ball on a post extends upwardly from the lower member. The spherical pivot ball is received in a spherical pivot socket on the upper member. Between the upper and lower members and surrounding the post and pivot ball is an annular resilient cushion member.

SUMMARY OF THE INVENTION

An artificial disc to replace a damaged spinal disc in a spinal column includes an upper retaining member having an outer surface engageable with a first vertebra of the spinal column and an inner surface. A lower retaining member has an outer surface engageable with a second vertebra of the spinal column and an inner surface. A resilient core interconnects the upper and lower retaining members. The resilient core has an upper surface affixed to the inner surface of the upper retaining member. The resilient core has a lower surface affixed to the inner surface of the lower retaining member. The resilient core has a surface extending from one of the upper and lower surfaces toward another of the upper and lower surfaces and at least partially defining an empty space extending from the one of the upper and lower surfaces.

In one embodiment of an artificial disc constructed in accordance with the invention, the upper and lower surfaces have recesses defining first and second empty spaces. In a second embodiment of the invention, the resilient core includes an opening extending from the upper surface to the lower surface to define the empty space.

BRIEF DESCRIPTION OF THE DRAWINGS

The foregoing and other features of the present invention will become apparent one skilled in the art to which the present invention relates upon consideration of the following description of the invention with reference to the accompanying drawings, in which:

FIG. 4 is a schematic sectional view of the artificial disc of FIG. 1 between adjacent vertebrae of a human spinal column;

FIG. 5 is a schematic sectional view of the artificial disc of FIG. 1 between adjacent vertebrae of the spinal column showing the spinal column in flexion;

DESCRIPTION OF THE INVENTION

Figure 1:
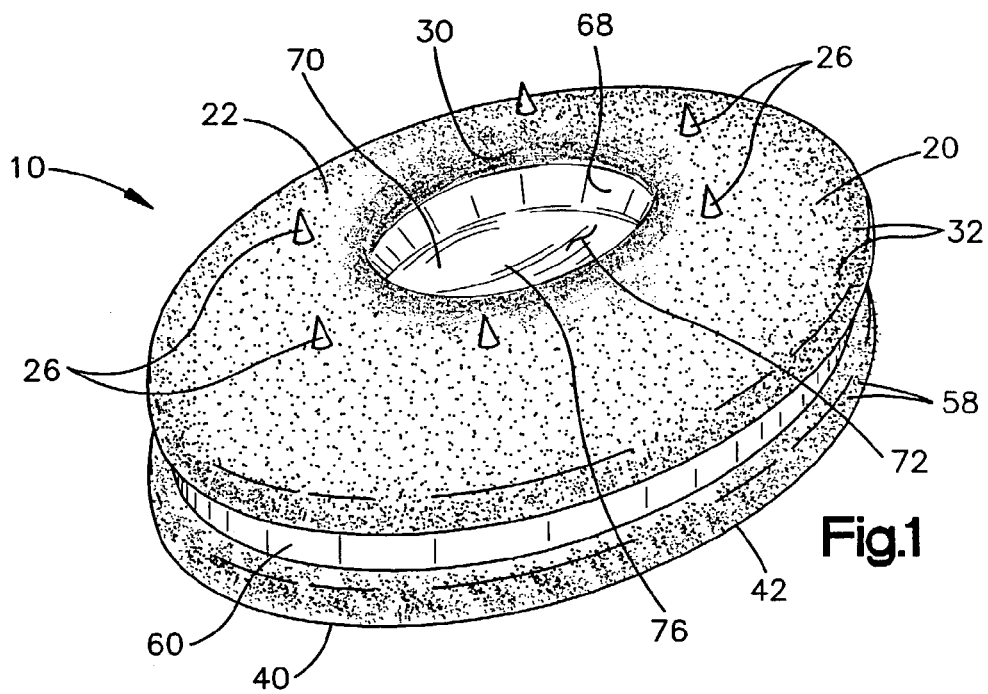
FIG. 1 is a pictorial view of an artificial disc constructed in accordance with a first embodiment of the present invention.

The present invention relates to an artificial disc to replace a damaged or degenerated spinal disc in a spinal column of a human. As representative of the present invention, FIG. 1 illustrates a first embodiment of an artificial disc 10. The artificial disc 10 (FIG. 4) is used to replace a damaged spinal disc between adjacent upper and lower vertebrae 12 and 14 of a human spinal column 16. The disc 10 has an oval-shaped outer periphery. It is contemplated that the outer periphery of the disc may have any desired shape.

Figure 2:
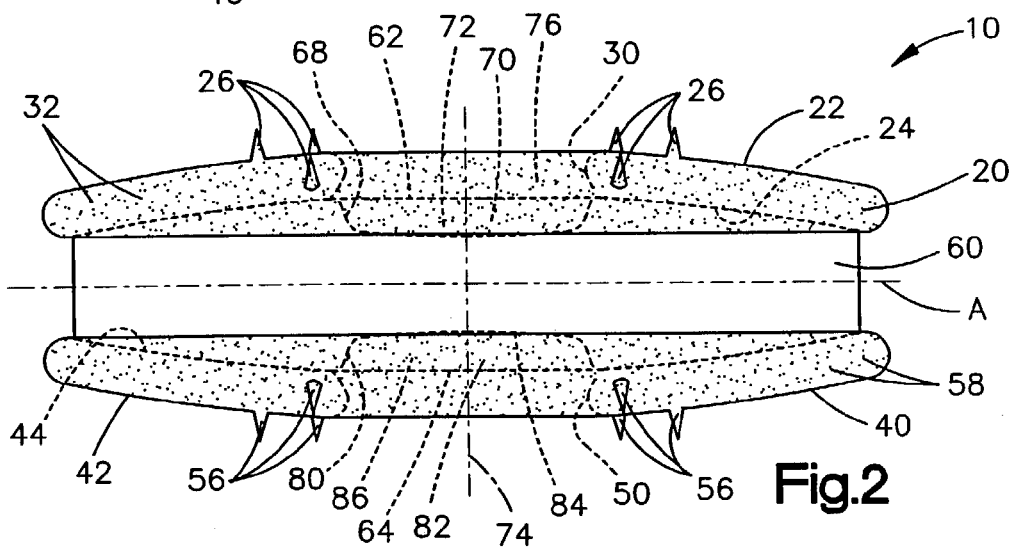
FIG. 2 is a schematic side view of the artificial disc of FIG. 1.
Figure 3:
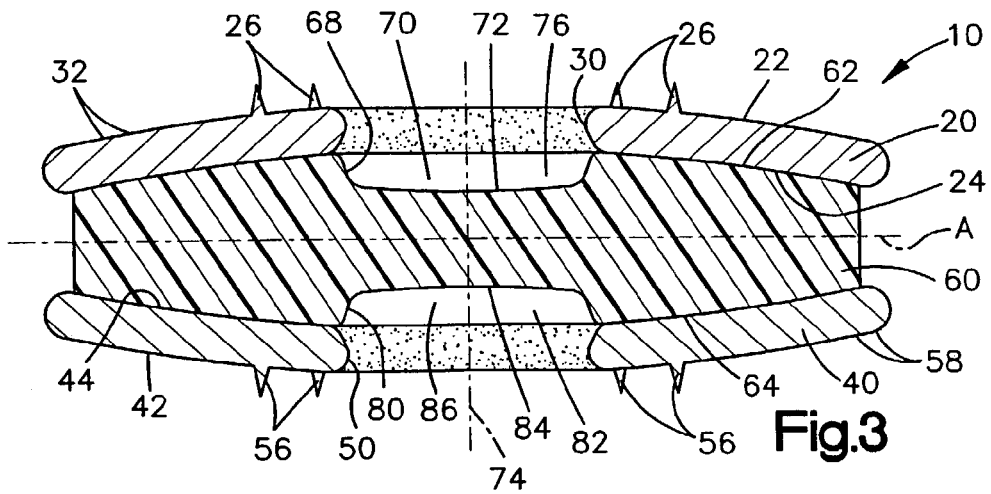
FIG. 3 is a sectional view of the artificial disc of FIG. 1.
Figure 6:
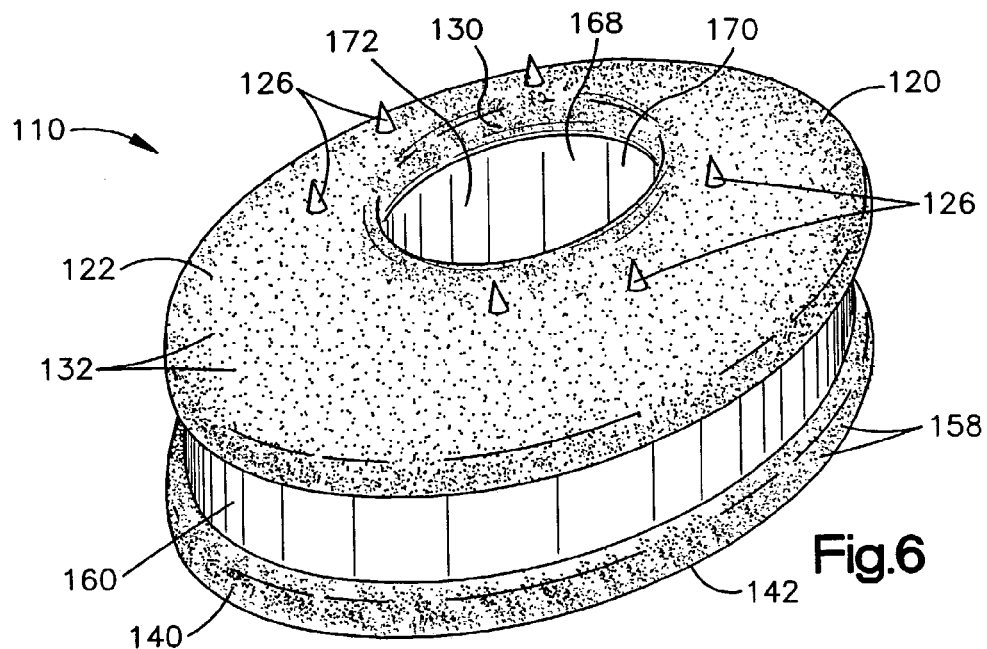
FIG. 6 is a pictorial view of an artificial disc constructed in accordance with a second embodiment of the present invention.

The artificial disc 10 (FIGS. 1–3) includes an upper retaining member 20, a lower retaining member 40, and a resilient core 60 interconnecting the two retaining members. The retaining members 20 and 40 are only interconnected by the core 60. The upper and lower retaining members 20 and 40 are identical to each other and the disc 10 is symmetrical about a horizontally extending plane A (FIGS. 2 and 3). The terms "upper" and "lower" are used herein with reference to the orientation of the disc 10 when it is implanted in the human body, as illustrated in FIG. 4, to distinguish the two identical retaining members for reference purposes.

The upper retaining member 20 is rigid and made of a biocompatible material such as a biocompatible metal or polymer. It is contemplated that the upper retaining member 20 could be made of a titanium alloy. The upper retaining member 20 (FIGS. 1–4) has an outer convex surface 22 engageable with the vertebra 12. An inner concave surface 24 of the upper retaining ring 20 is affixed or bonded to the resilient core 60.

The upper retaining member 20 has an axially extending opening 30. The opening 30 extends through the outer surface 22 and the inner surface 24. The resilient core 60 may deflect into the opening 30 upon relative movement between the upper and lower retaining members 20 and 40, such as when the spine 16 is bent in flexion, as shown in FIG. 5. The core 60 expends energy when the core deflects into the opening 30 to limit the amount of stress in the core. It is contemplated that the opening 130 may have any desired size and shape. It is also contemplated that the upper retaining member 20 may not include an opening 30.

Projections 26 extend from the outer surface 22 of the upper retaining member 20. The projections 26 (FIGS. 4 and 5) engage the vertebra 12 to retain the disc 10 in position between the vertebrae 12 and 14. The outer surface 22 of the upper retaining member 20 also has beads 32 sintered on the outer surface to further retain the disc 10 between the vertebrae 12 and 14.

The lower retaining member 40 (FIGS. 2–4) is identical in configuration to the upper retaining member 20. The lower retaining member 40 is rigid and made from the same material as the upper retaining member 20, such as a titanium alloy. The lower retaining member 40 has a convex outer surface 42 engageable with the vertebra 14. An inner concave surface 44 of the lower retaining member 40 is affixed or bonded to the resilient core 60.

The lower retaining member 40 has an axially extending opening 50. The opening 50 extends through the outer surface 42 and the inner surface 44. The resilient core 60 may deflect into the opening 50 upon relative movement between the upper and lower retaining members 20 and 40, as shown in FIG. 5. The core 60 expends energy when the core deflects into the opening 50 to limit the amount of stress in the core. It is contemplated that the opening 50 may have any desired size and shape. It is also contemplated that the lower retaining member 40 may not include an opening 50.

Projections 56 extend from the outer surface 42 of the lower retaining member 40. The projections 56 (FIGS. 4 and 5) engage the vertebra 14 to retain the disc 10 in position between the vertebrae 12 and 14. The outer surface 42 also has beads 58 sintered on the outer surface to further retain the disc 10 between the vertebrae 12 and 14.

The resilient core 60 is made of a urethane silicon blend and manufacturer by The Polymer Technology Group located in Berkley, Calif. The resilient core 60 may be adhered or bonded to the upper and lower retaining members 20 and 40 in any manner known in the art. It is contemplated that the resilient core 60 could be insert molded, transfer molded, or injection molded between the upper and lower retaining members 20 and 40. The core 60 may be molded between the upper and lower retaining members 20 and 40 by injecting the material for the core through one of the openings 30 or 50 in the upper and lower retaining members. It is contemplated that the resilient core 60 may be wedge-shaped so that the upper retaining member 20 is spaced from the lower retaining member 40 a first distance adjacent one side of the disc 10 and spaced from the lower retaining member 40 a second distance adjacent another side of the disc 10.

The core 60 has an upper convex surface 62. The upper convex surface 62 is affixed to the concave inner surface 24 of the upper retaining member 20. A convex lower surface 64 of the core 60 is affixed to the concave inner surface 44 of the lower retaining member 40. The concave inner surfaces 24 and 44 limit the amount of stress in the core 60 upon relative movement of the upper and lower retaining members 20 and 40.

The core 60 (FIGS. 1–4) has a tapered or frustoconical surface 68 extending from the upper convex surface 62 toward the lower convex surface 64. The surface 68 at least partially defines an empty space 70 that extends from the upper convex surface 62 toward the lower convex surface 64. The surface 68 extends from the upper convex surface 62 to a surface 72 that extends transverse to the axis 74 of the disc 10 and generally parallel to the plane A. The surfaces 68 and 70 define a concave recess 76 in the upper surface that is coaxial with the disc 10 and defines the empty space 70. The resilient core 60 deflects into the empty space 70 defined by the recess 76 upon relative movement between the upper and lower retaining members 20 and 40, as shown in FIG. 5. The core 60 expends energy when the core deflects into the empty space 70 to limit the amount of stress in the core. It is contemplated that the recess 76 may have any desired shape or depth and be in any desired location in the upper surface 62. It is also contemplated that the upper surface 62 may have any number of recesses.

A tapered or frustoconical surface 80 extends from the lower convex surface 64 of the core 60 toward the upper convex surface 62. The surface 80 at least partially defines an empty space 82 extending from the lower convex surface 64 toward the upper convex surface 62. The surface 80 extends from the lower surface 64 to a surface 84 extending transverse to the axis 74 and generally parallel to the plane A and the surface 72. The surfaces 80 and 84 define a concave recess 86 in the lower surface 64 that is coaxial with the disc 10 and defines the empty space 82. The resilient core 60 deflects into the empty space 82 upon relative movement between the upper and lower retaining members 20 and 40, as shown in FIG. 5. The core 60 expends energy when the core deflects into the empty space 82 to limit the amount of stress in the core. It is contemplated that the recess 86 may have any desired shape or depth and be in any desired location in the upper surface 62. It is also contemplated that the upper surface 62 may have any number of recesses.

When the disc 10 (FIGS. 4 and 5) is in use in the spinal column 16, the upper retaining member 20 is affixed to the vertebra 12. The projections 26, the beads 32, and the convex surface 22 resist relative movement between the upper retaining member 20 and the vertebra 12. The lower retaining member 40 is affixed to the vertebra 14. The projections 56, the beads 58, and the convex surface 42 resist relative movement between the lower retaining member 40 and the vertebra 14. When the upper retaining members 20 and 40 move relative to each other, such as when the spine 16 is bent in flexion, as shown in FIG. 5, the resilient core 60 deflects into the empty spaces 70 and 82 in the core. It is contemplated that the core 60 may deflect into the openings 30 and 50 in the retaining members 20 and 40. Accordingly, the core 60 expends energy to reduce stress in the core upon relative movement of the upper and lower retaining members 20 and 40 to provide a relatively long fatigue life for the core 60.

An artificial disc 110 constructed in accordance with a second embodiment of the present invention is illustrated in FIGS. 6–10. The artificial disc 110 (FIG. 9) is used to replace a damaged spinal disc between adjacent upper and lower vertebrae 112 and 114 of a human spinal column 116. The disc 110 has an oval-shaped outer periphery. It is contemplated that the outer periphery of the disc may have any desired shape.

Figure 7:
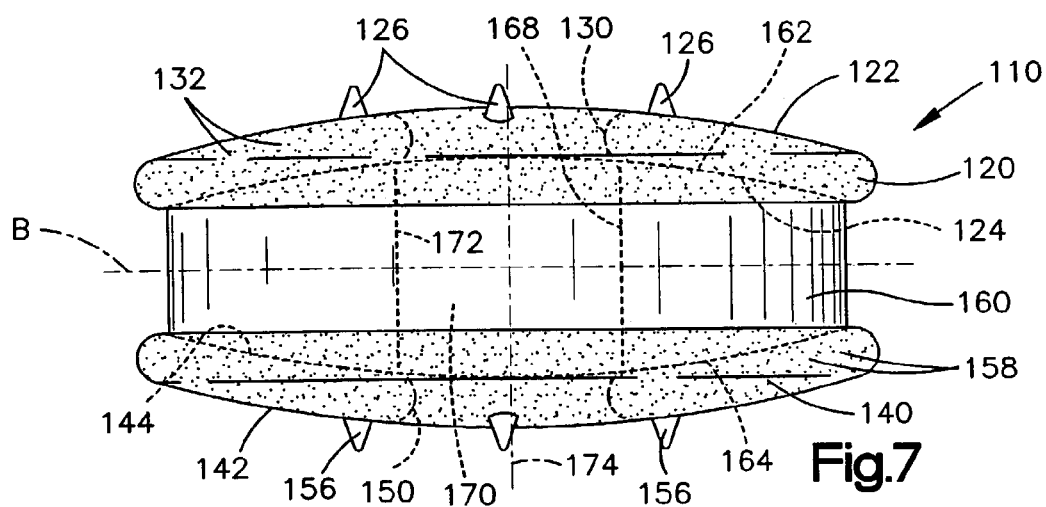
FIG. 7 is a schematic side view of the artificial disc of FIG. 6.
Figure 8:
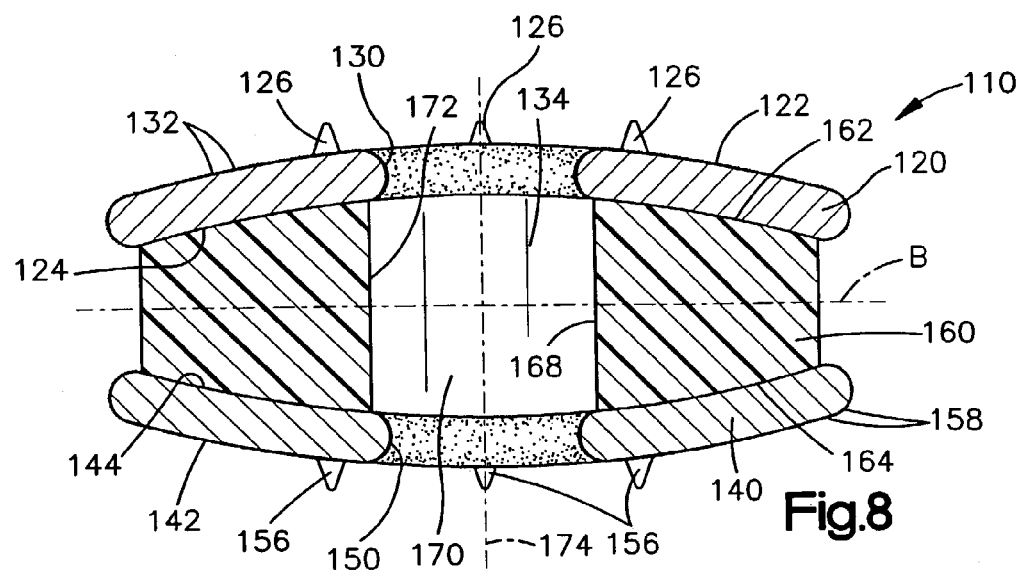
FIG. 8 is a sectional view of the artificial disc of FIG. 6.
Figure 9:
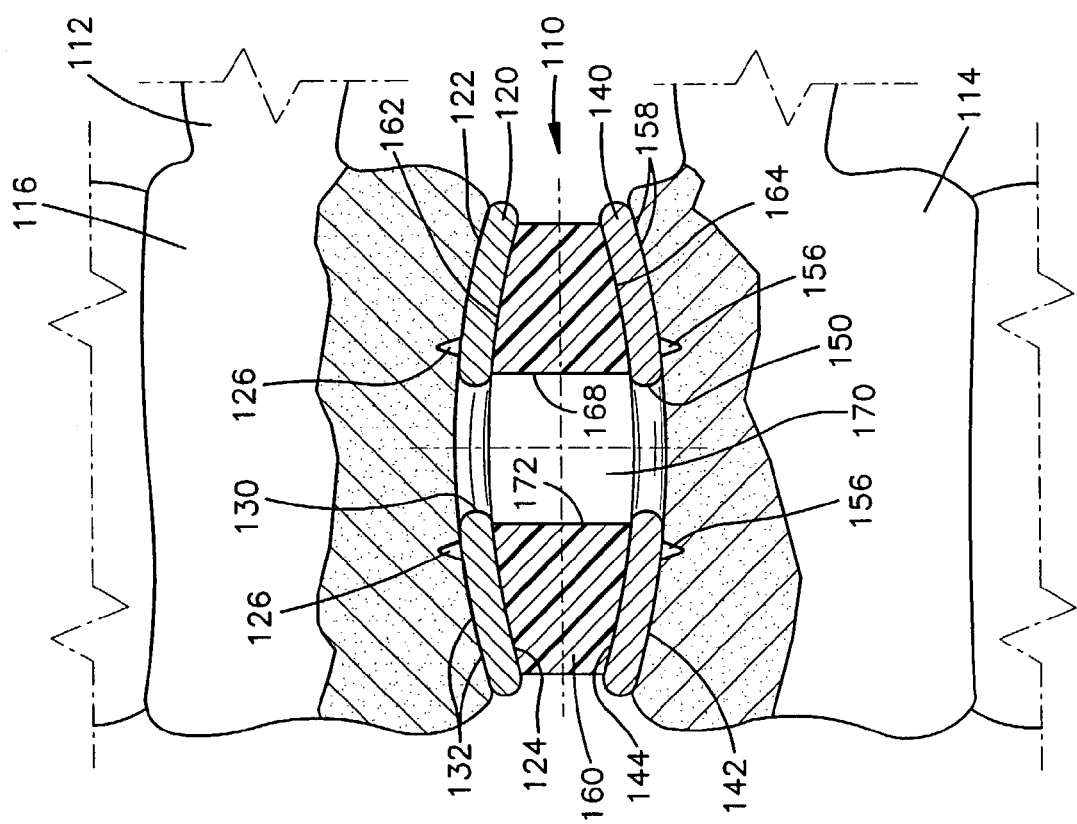
FIG. 9 is a schematic sectional view of the artificial disc of FIG. 6 between adjacent vertebrae of a human spinal column.

The artificial disc 110 (FIGS. 6–8) includes an upper retaining member 120, a lower retaining member 140, and a resilient core 160 interconnecting the two retaining members. The retaining members 120 and 140 are only interconnected by the core 160. The upper and lower retaining members 120 and 140 are identical to each other and the disc 110 is symmetrical about a horizontally extending plane B (FIGS. 7 and 8). The terms "upper" and "lower" are used herein with reference to the orientation of the disc 110 when it is implanted in the human body, as illustrated in FIG. 9, to distinguish the two identical retaining members for reference purposes.

The upper retaining member 120 is rigid and made of a biocompatible material such as a biocompatible metal or polymer. It is contemplated that the upper retaining member 120 could be made of a titanium alloy. The upper retaining member 120 (FIGS. 6–9) has an outer convex surface 122 engageable with the vertebra 112. An inner concave surface 124 of the upper retaining member 120 is affixed or bonded to the resilient core 160.

The upper retaining member 120 has an axially extending opening 130. The opening 130 extends through the outer surface 122 and the inner surface 124. The resilient core 160 may deflect into the opening 130 upon relative movement between the upper and lower retaining members 120 and 140, such as when the spine 116 is bent in flexion. The core 160 expends energy when the core deflects into the opening 130 to limit the amount of stress in the core. It is contemplated that the opening 130 may have any desired size and shape. It is also contemplated that the upper retaining member 120 may not include an opening 130.

Projections 126 extend from the outer surface 122 of the upper retaining member 120. The projections 126 (FIGS. 9 and 10) engage the vertebra 112 to retain the disc 110 in position between the vertebrae 112 and 114. The outer surface 122 of the upper retaining member 120 also has beads 132 sintered on the outer surface to further retain the disc 110 between the vertebrae 112 and 114.

The lower retaining member 140 (FIGS. 7–9) is identical in configuration to the upper retaining member 120. The lower retaining member 140 is rigid and made from the same material as the upper retaining member 120, such as a titanium alloy. The lower retaining member 140 has a convex outer surface 142 engageable with the vertebra 114. An inner concave surface 144 of the lower retaining member 140 is affixed or bonded to the resilient core 160. The lower retaining member 140 has an axially extending opening 150. The opening 150 extends through the outer surface 142 and the inner surface 144. The resilient core 160 may deflect into the opening 150 upon relative movement between the upper and lower retaining members 120 and 140. The core 160 expends energy when the core deflects into the opening 150 to limit the amount of stress in the core. It is contemplated that the opening 150 may have any desired size and shape. It is also contemplated that the lower retaining member 140 may not include an opening 150.

Projections 156 extend from the outer surface 142 of the lower retaining member 140. The projections 156 (FIGS. 9 and 10) engage the vertebra 114 to retain the disc 110 in position between the vertebrae 112 and 114. The outer surface 142 also has beads 158 sintered on the outer surface to further retain the disc 110 between the vertebrae 112 and 114.

The resilient core 160 is made of a urethane silicon blend and manufactured by The Polymer Technology Group located in Berkley, Calif. The resilient core 160 may be adhered or bonded to the upper and lower retaining members 120 and 140 in any manner known in the art. It is contemplated that the resilient core 160 could be insert molded, transfer molded, or injection molded between the upper and lower retaining members 120 and 140. The resilient core 160 may be molded between the upper and lower retaining members 120 and 140 by injecting the material for the core through one of the openings 130 or 150 in the upper and lower retaining members. It is contemplated that the resilient core 160 could be wedged-shaped so that the upper retaining member 120 may be spaced from the lower retaining member 140 a first distance adjacent one side of the disc 110 and spaced from the lower retaining member a second distance adjacent another side of the disc 110.

The resilient core 160 has an upper convex surface 162. The upper convex surface 162 is bonded to the concave inner surface 124 of the upper retaining member 120. A convex lower surface 164 of the resilient core 160 is bonded to the concave inner surface 144 of the lower retaining member 140. The concave inner surfaces 124 and 144 limit the amount of stress in the core 160 upon relative movement between the upper and lower retaining members 120 and 140.

Figure 10:
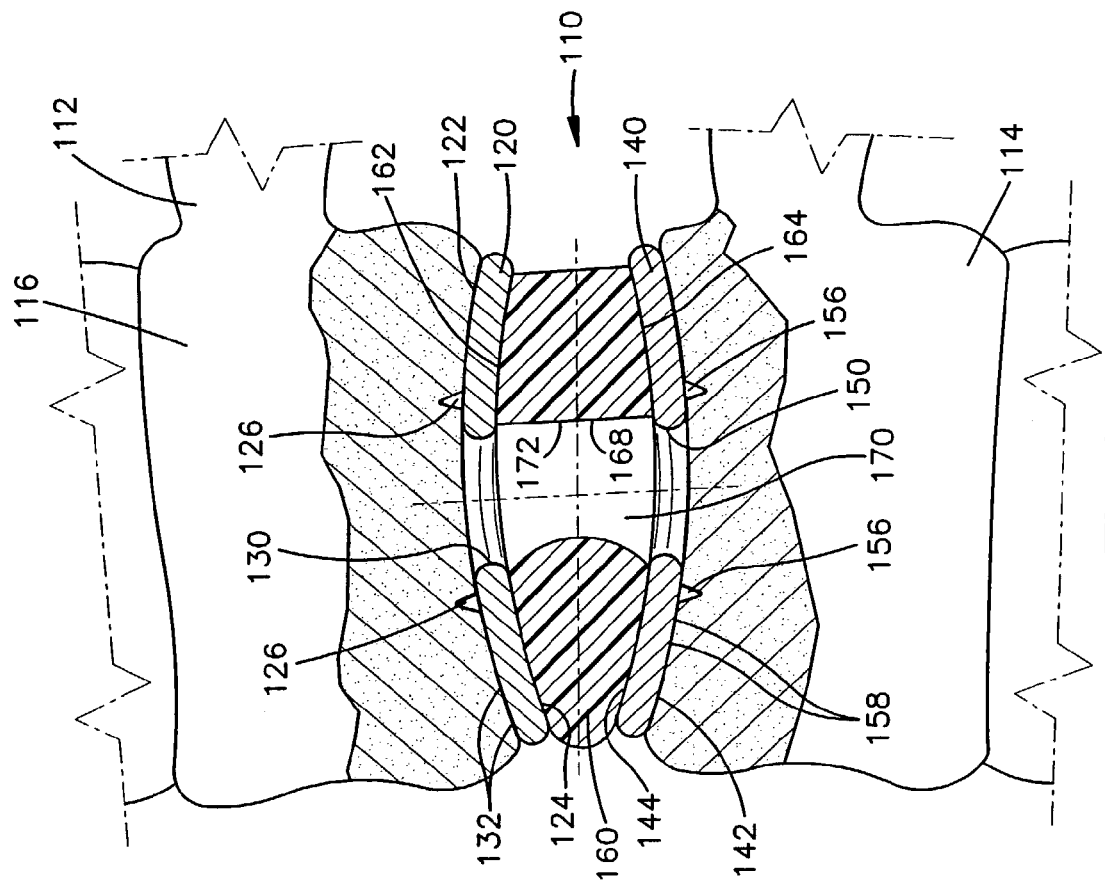
FIG. 10 is a schematic sectional view of the artificial disc of FIG. 6 between adjacent vertebrae of the spinal column showing the spinal column in flexion.

The resilient core 160 has a cylindrical surface 168 extending from the upper surface 162 to the lower surface 164. The cylindrical surface 168 defines an empty space 170 in the core 160 extending from the upper surface 162 to the lower surface 164. The cylindrical surface 168 is coaxial with an axis 174 of the disc 110. The resilient core 160 deflects into the empty space 170 upon relative movement between the upper and lower retaining members 120 and 140, as shown in FIG. 10. The core 160 expends energy when the core deflects into the empty space 170 to limit the amount of stress in the core. It is contemplated that the opening 172 may have any desired shape and be in any desired location in the core 160. It is also contemplated that the core 160 may have any number of openings extending from the upper surface 162 to the lower surface 164.

When the disc 110 (FIGS. 9 and 10) is in use in the spinal column 116, the upper retaining member 120 is affixed to the vertebra 112. The projections 126, the beads 132, and the convex surface 122 resist relative movement between the upper retaining member 120 and the vertebra 112. The lower retaining member 140 is affixed to the vertebra 114. The projections 156, the beads 158, and the convex surface 142 resist relative movement between the lower retaining member 140 and the vertebra 114. When the upper and lower retaining members 120 and 140 move relative to each other, such as when the spine 116 is bent in flexion, as shown in FIG. 10, the resilient core 160 deflects into the empty space 170 in the core. Accordingly, the core 160 expends energy to reduce stress in the core upon relative movement between the upper and lower retaining members 120 and 140 to provide a relatively long fatigue life for the core 160.

From the above description of the invention, those skilled in the art will perceive improvements, changes and modifications. Such improvements, changes and modifications within the skill of the art are intended to be covered by the appended claims.

Having described the invention, the following is claimed:

1. An artificial disc to replace a damaged spinal disc in a spinal column, said artificial disc comprising:
   an upper retaining member having an outer surface engageable with a first vertebra of the spinal column and an inner surface;
   a lower retaining member having an outer surface engageable with a second vertebra of the spinal column and an inner surface; and
   a resilient core interconnecting said upper and lower retaining members, said resilient core having an upper surface immovably affixed to said inner surface of said upper retaining member, said resilient core having a lower surface immovably affixed to said inner surface of said lower retaining member, said resilient core having a surface extending from one of said upper and lower surfaces toward another of said upper and lower surfaces and at least partially defining an empty space extending from said one of said upper and lower surfaces.

2. An artificial disc as defined in claim 1 wherein one of said upper and lower surfaces includes a recess defining said empty space.

3. An artificial disc as defined in claim 2 wherein said surface extending from said one of said upper and lower surfaces extends to a second surface extending transverse to an axis of said disc to define said recess.

4. An artificial disc as defined in claim 3 wherein said surface extending from one of said upper and lower surfaces of said resilient core extends from said upper surface to said second surface to define said recess.

5. An artificial disc as defined in claim 2 wherein said recess is coaxial with said disc.

6. An artificial disc as defined in claim 1 wherein said surface extends from said upper surface of said resilient core toward said lower surface to at least partially define a first empty space extending from said upper surface toward said lower surface, said resilient core having a second surface extending from said lower surface toward said upper surface to at least partially define a second empty space extending from said lower surface toward said upper surface.

7. An artificial disc as defined in claim 6 wherein said upper surface of said resilient core has a first recess defining said first empty space and said lower surface of said resilient core has a second recess defining said second empty space.

8. An artificial disc as defined in claim 7 wherein said resilient core includes third and fourth surfaces extending transverse to an axis of said disc, said first surface extending from said upper surface to said third surface to define said first recess and said second surface extending from said lower surface to said fourth surface to define said second recess.

9. An artificial disc as defined in claim 8 wherein said third and fourth surfaces extend generally parallel to each other.

10. An artificial disc as defined in claim 8 wherein said first and second recesses are coaxial with said disc.

11. An artificial disc as defined in claim 1 wherein said resilient core includes an opening extending from said upper surface to said lower surface to define said empty space.

12. An artificial disc as defined in claim 11 wherein said surface is cylindrical and extends from said upper surface of said core to said lower surface of said core to define said opening.

13. An artificial disc as defined in claim 12 wherein said cylindrical surface is coaxial with said disc.

14. An artificial disc as defined in claim 1 wherein said upper and lower retaining members are interconnected only by said core.

15. An artificial disc as defined in claim 1 wherein one of said upper and lower retaining members has an opening extending through said inner and outer surfaces of said one of said upper and lower retaining members.

16. An artificial disc as defined in claim 15 wherein said opening extending through said inner and outer surfaces of said one of said upper and lower retaining members is axially aligned with said empty space.

17. An artificial disc as defined in claim 1 wherein said upper retaining member has an opening extending through said inner and outer surfaces of said upper retaining member, said lower retaining member having an opening extending through said inner and outer surfaces of said lower retaining member.

18. An artificial disc as defined in claim 15 wherein said opening extends axially through said one of said upper and lower retaining members.

19. An artificial disc as defined in claim 1 wherein said upper and lower surfaces of said resilient core are convex and said inner surfaces of said upper and lower retaining members are concave.

20. An artificial disc as defined in claim 1 wherein said outer surfaces of said upper and lower retaining members are convex.

21. An artificial disc as defined in claim 20 wherein said inner surfaces of said upper and lower retaining members are concave, said upper and lower surfaces of said resilient core being convex.

22. An artificial disc as defined in 1 wherein one of said upper and lower retaining members has an opening extending through said inner surface of said one of said upper and lower retaining members.

23. An artificial disc as defined in claim 1 wherein said upper and lower retaining members have openings extending through said inner surfaces of said upper and lower retaining members.

24. An artificial disc as defined in claim 22 wherein said resilient core deflects into said opening extending through said inner surface of said one of said upper and lower retaining members.

25. An artificial disc as defined in claim 1 wherein said resilient core deflects into said empty space upon relative movement between said upper and lower retaining members.

* * * * *